United States Patent
Takeda

(10) Patent No.: US 10,852,933 B2
(45) Date of Patent: Dec. 1, 2020

(54) MEDICAL IMAGE DISPLAY APPARATUS

(71) Applicant: KONICA MINOLTA, INC., Tokyo (JP)

(72) Inventor: Osamu Takeda, Kokubunji (JP)

(73) Assignee: KONICA MINOLTA, INC., Tokyo (JP)

(*) Notice: Subject to any disclaimer, the term of this patent is extended or adjusted under 35 U.S.C. 154(b) by 52 days.

(21) Appl. No.: 15/844,103

(22) Filed: Dec. 15, 2017

(65) Prior Publication Data
US 2018/0203581 A1 Jul. 19, 2018

(30) Foreign Application Priority Data

Jan. 13, 2017 (JP) ................. 2017-003758

(51) Int. Cl.
G06F 3/0488 (2013.01)
A61B 8/00 (2006.01)
G06F 3/0481 (2013.01)
A61B 5/107 (2006.01)
A61B 5/00 (2006.01)

(52) U.S. Cl.
CPC ............ *G06F 3/0488* (2013.01); *A61B 8/461* (2013.01); *A61B 8/465* (2013.01); *A61B 8/469* (2013.01); *G06F 3/0481* (2013.01); *A61B 5/1075* (2013.01); *A61B 5/7475* (2013.01)

(58) Field of Classification Search
CPC ..... G06F 3/0488; G06F 3/0481; A61B 8/469; A61B 8/465
See application file for complete search history.

(56) References Cited

U.S. PATENT DOCUMENTS

| 10,631,825 | B2 | 4/2020 | Lee et al. | |
| 10,687,780 | B2 | 6/2020 | Fukai et al. | |
| 2002/0067346 | A1* | 6/2002 | Mouton | G06F 3/04886 345/173 |
| 2014/0121524 | A1* | 5/2014 | Chiang | A61B 8/463 600/459 |
| 2014/0276057 | A1 | 9/2014 | Lee et al. | |
| 2015/0049039 | A1 | 2/2015 | Lee et al. | |
| 2015/0164474 | A1 | 6/2015 | Lee et al. | |
| 2017/0123598 | A1* | 5/2017 | Phan | G06F 3/0482 |
| 2017/0153785 | A1* | 6/2017 | Glaser | G06F 3/04812 |

FOREIGN PATENT DOCUMENTS

| JP | 2009213507 A | 9/2009 |
| JP | 2010142563 A | 7/2010 |
| JP | 2012019824 A | 2/2012 |
| JP | 2014097127 A | 5/2014 |
| JP | 2016516465 A | 6/2016 |

OTHER PUBLICATIONS

Japanese Office Action dated Jul. 21, 2020 (and English translation thereof) issued in Japanese Application No. 2014003758.

* cited by examiner

*Primary Examiner* — Seth A Silverman
(74) *Attorney, Agent, or Firm* — Holtz, Holtz & Volek PC

(57) ABSTRACT

A medical image display apparatus includes the following. A touch operating unit receives a touch input on a display screen of a display which displays a medical image. A display controller moves a movement operation element in response to the touch input to a region including the medical image except for the movement operation element displayed on the display screen.

8 Claims, 11 Drawing Sheets

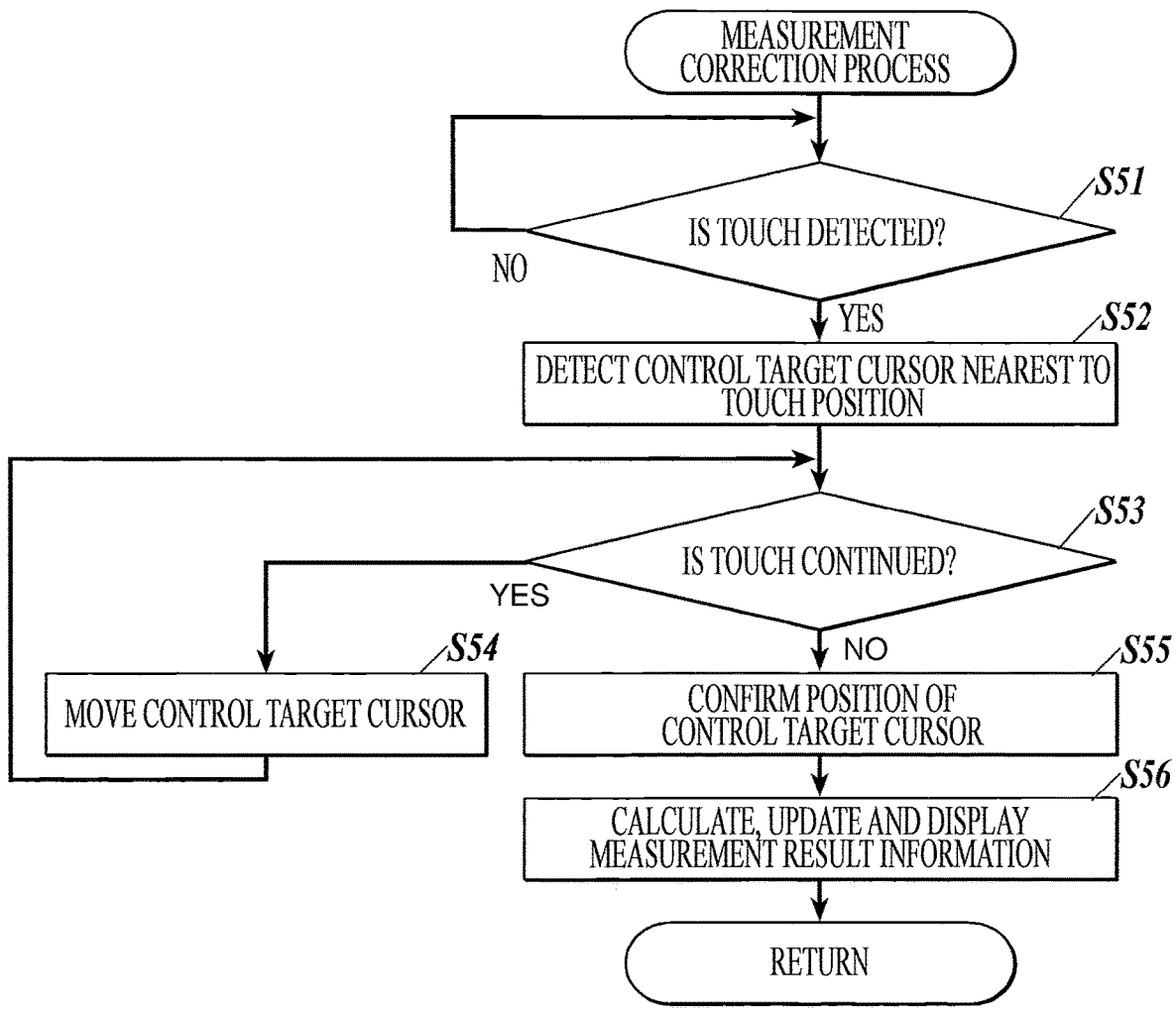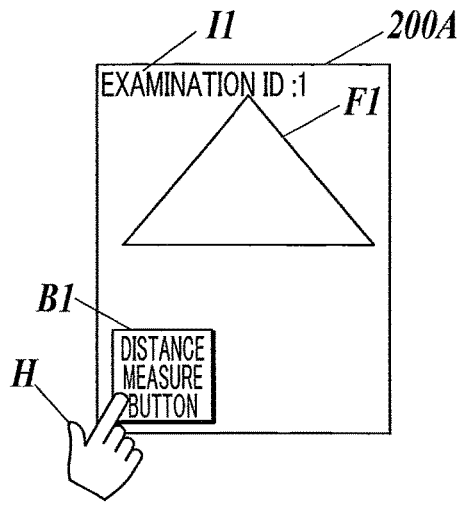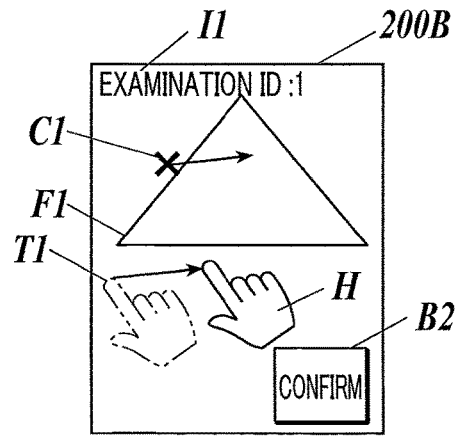

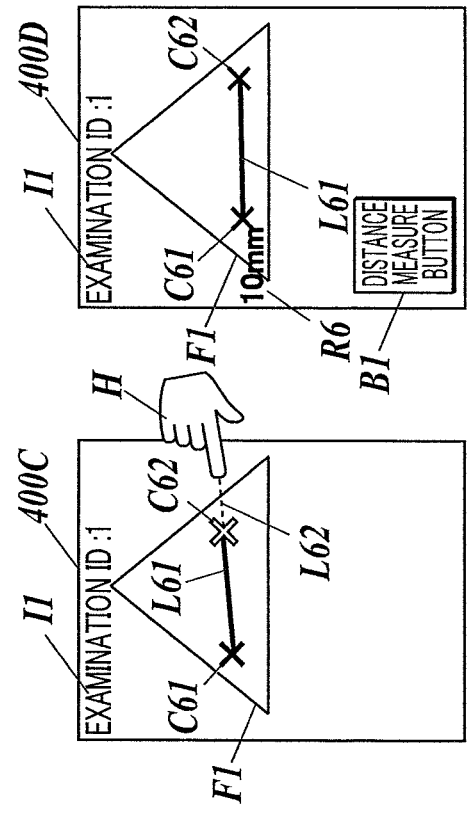

MEDICAL IMAGE DISPLAY APPARATUS

BACKGROUND

1. Technological Field

The present invention relates to a medical image display apparatus.

2. Description of the Related Art

In ultrasound diagnosis, by a simple operation such as placing an ultrasound probe against a surface of a body, a heartbeat of a heart or a movement of a fetus can be observed as an ultrasound image. Moreover, since ultrasound diagnosis is very safe, examination can be performed repeatedly. There is a known ultrasound diagnostic apparatus which is used for ultrasound diagnosis and which generates and displays an ultrasound image.

There is also a known ultrasound diagnostic apparatus which includes a touch panel on a display screen of a display, which receives touch operation from an operator (examiner (physician, technician)) through a touch panel and which performs movement of the cursor as the movement operation element for measurement of a length of a measurement target such as a lesion in an ultrasound image in response to a touch operation. However, when the user attempts to directly operate the cursor by touching, the cursor is hidden by the finger, and the cursor cannot be set in an accurate position. Moreover, when buttons pointing up, down, left, and right in a specific region of the display screen are provided and the cursor is moved by such buttons, intuitive feel of operation by touching is lost.

In view of the above, there is a known ultrasound diagnostic apparatus which collectively displays a caliper as a marker showing a target spot and touch buttons corresponding to the caliper maintaining their relative positions, and the caliper moves according to the direct touch of the touch buttons (for example, Japanese Patent Application Laid-Open Publication No. 2012-19824).

There is also a known ultrasound diagnostic apparatus which includes in a portion of the display screen a touchpad area different from the ultrasound image region and the mouse cursor is moved according to touch operation of the touchpad area (for example, Japanese Patent Application Laid-Open Publication No. 2010-142563).

However, according to the ultrasound diagnostic apparatus as shown in Japanese Patent Application Laid-Open Publication No. 2012-19824, since the touch buttons corresponding to the caliper is displayed from the beginning and the relative positions are fixed, the relation of the positions between the touch buttons and the caliper do not always meet the preference of the operator. When the caliper is moved while referring to an image portion other than a measurement target, the touch buttons may overlap with an image portion other than the measurement target. Therefore, the operability is not always satisfactory Moreover, according to the ultrasound diagnostic apparatus as shown in Japanese Patent Application Laid-Open Publication No. 2010-142563, when the cursor is moved according to a relation of relative positions by operating the specific touchpad area, the relation of the positions does not always meet the preference of the operator. Therefore, the operability is not always satisfactory.

SUMMARY

An object of the present invention, which has been made in view of these problems described above, is to enhance operability and accuracy of movement of a movement operation component by intuitive operation by touching a desired position.

To achieve at least one of the abovementioned objects, according to an aspect of the present invention, the medical image display apparatus reflecting one aspect of the present invention includes a touch operating unit which receives a touch input on a display screen of a display which displays a medical image; and a display controller which moves a movement operation element in response to the touch input to a region including the medical image except for the movement operation element displayed on the display screen.

BRIEF DESCRIPTION OF THE DRAWINGS

The advantages and features provided by one or more embodiments of the invention will become more fully understood from the detailed description given hereinbelow and the appended drawings which are given by way of illustration only, and thus are not intended as a definition of the limits of the present invention.

FIG. 5 is a flowchart showing a measurement correction process.

FIG. 6A is a diagram showing a first display screen.
FIG. 6B is a diagram showing a second display screen.

FIG. 13A is a diagram showing a sixteenth display screen.
FIG. 13B is a diagram showing a seventeenth display screen.
FIG. 13C is a diagram showing an eighteenth display screen.
FIG. 13D is a diagram showing a nineteenth display screen.

DETAILED DESCRIPTION OF EMBODIMENTS

Hereinafter, the first to third embodiments of the present invention are described in detail in order with reference to the enclosed drawings. However, the scope of the invention is not limited to the illustrated examples.

First Embodiment

Figure 1:
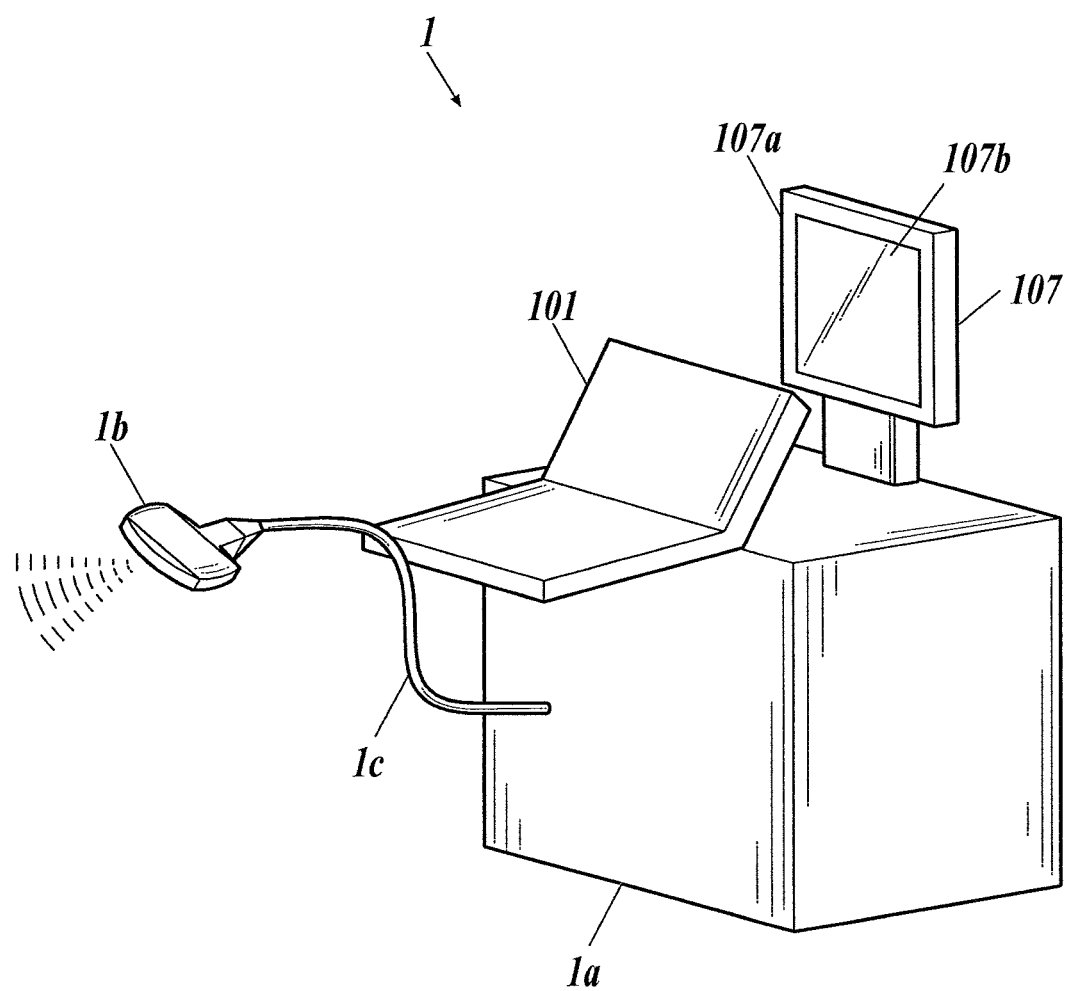
FIG. 1 is a diagram showing an external view of an ultrasound diagnostic apparatus according to an embodiment of the present invention.
Figure 2:
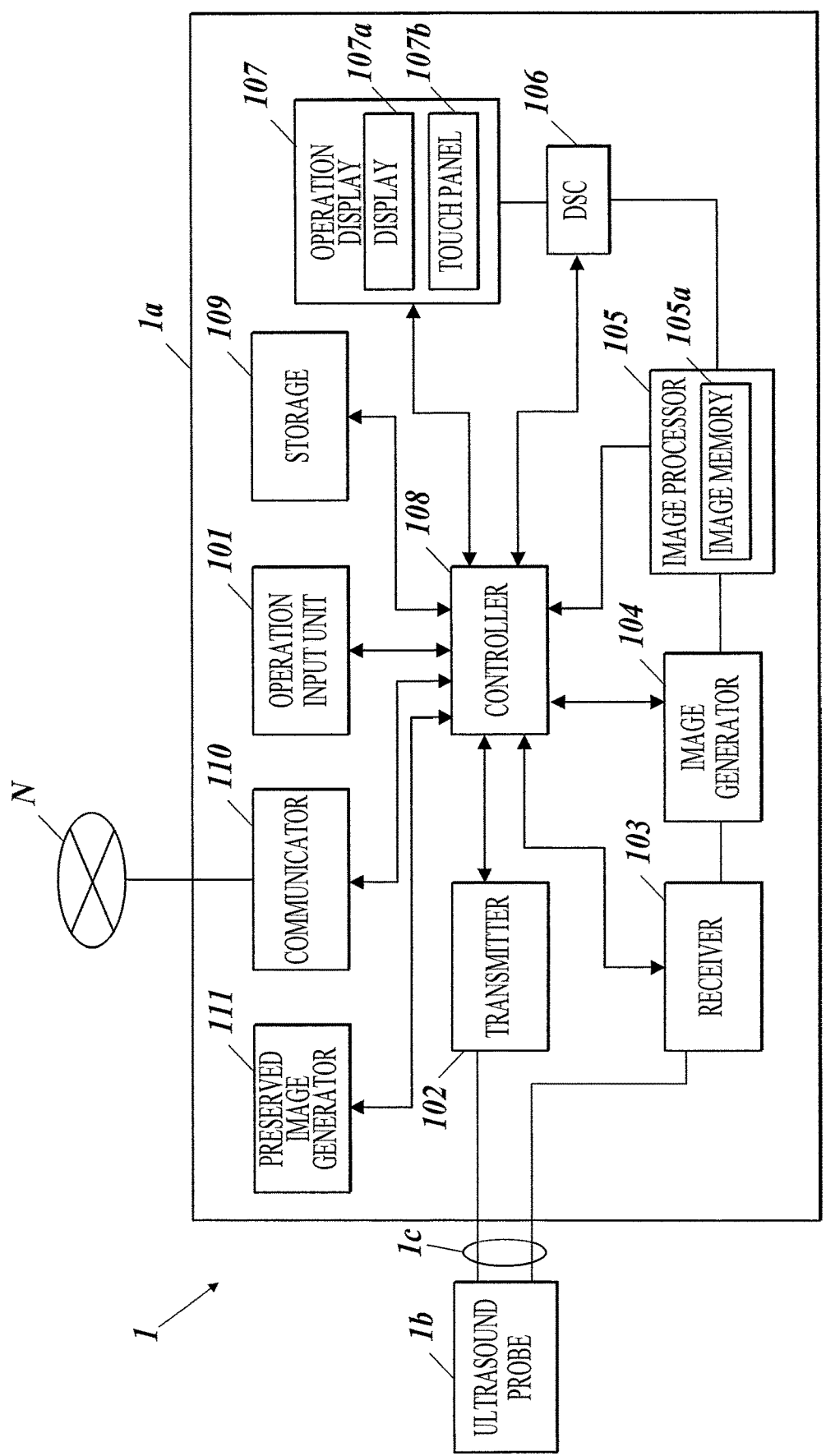
FIG. 2 is a block diagram showing a functional configuration of an ultrasound diagnostic apparatus.

The first embodiment of the present invention is described with reference to FIG. 1 to FIG. 8C. First, with reference to FIG. 1 and FIG. 2, the configuration of the apparatus of the present embodiment is described. FIG. 1 is a diagram showing an external view of the ultrasound diagnostic apparatus 1 of the present embodiment. FIG. 2 is a block diagram showing a functional configuration of the ultrasound diagnostic apparatus 1.

The ultrasound diagnostic apparatus 1 of the present embodiment shown in FIG. 1 and FIG. 2 is provided in a medical facility such as a hospital. The ultrasound diagnostic apparatus 1 includes an ultrasound diagnostic apparatus main body 1a and an ultrasound probe 1b. The ultrasound probe 1b transmits ultrasound (transmitting ultrasound) to a subject such as live body of a patient (not shown) and receives reflected waves (reflected ultrasound: echo) of the ultrasound reflected from the subject. The ultrasound diagnostic apparatus main body 1a is connected to the ultrasound probe 1b through a cable 1c. The ultrasound diagnostic apparatus main body 1a transmits an electric driving signal to the ultrasound probe 1b so that the ultrasound probe 1b transmits the transmitting ultrasound to the subject. An electric signal is generated in the ultrasound probe 1b according to the reflected ultrasound received in the ultrasound probe 1b from the subject and the ultrasound diagnostic apparatus main body 2a images an internal state of the subject as the ultrasound image according to the received signal which is the generated electric signal.

The ultrasound probe 1b includes a transducer including a piezoelectric device and a plurality of transducers are aligned in a one-dimensional array in an orientation direction. For example, according to the present embodiment, an ultrasound probe 1b including 192 transducers is used. The transducers may be arranged in a two-dimensional array. The number of transducers can be freely set. According to the present embodiment, an electronic scanning probe using a convex scanning method is employed as the ultrasound probe 1b. Alternatively, an electronic scanning method or a mechanical scanning method can be employed. Further, a linear scanning method, a sector scanning method or a convex scanning method can be employed.

As shown in FIG. 2, for example, the ultrasound diagnostic apparatus main body 1a includes, an operation input unit 101, a transmitter 102, a receiver 103, an image generator 104, an image processor 105, a DSC (Digital Scan Converter) 106, an operation display 107, a controller 108 as a display controller and calculator, a storage 109, a communicator 110, and a preserved image generator 111.

For example, the operation input unit 101 includes various switches, buttons, a trackball, mouse, and a keyboard to input commands to instruct start of examination of the patient as the subject or data such as subject information as personal information of the subject and outputs operation information according to the input to the controller 108.

The transmitter 102 is a circuit which, according to control from the controller 108, supplies an electric driving signal through the cable 1c to the ultrasound probe 1b so that the ultrasound probe 1b generates the transmitting ultrasound. The transmitter 102 includes, for example, a clock generating circuit, a delaying circuit, and a pulse generating circuit. The clock generating circuit is a circuit which generates a clock signal to determine the transmitting timing and the transmitting frequency of the driving signal. The delaying circuit is a circuit for setting the delaying time of the transmitting timing of the driving signal for each individual path corresponding to each transducer so that the transmission of the driving signal is delayed for the set delay time to focus the transmitting beam including the transmitting ultrasound. The pulse generating circuit is a circuit to generate the pulse signal as the driving signal at a predetermined cycle. The transmitter 102 configured as described above drives a portion (for example, 64) among the continuous transducers (for example, 192) arranged in the ultrasound probe 1b and generates the transmitting ultrasound. Then, the transmitter 102 scans shifting the driven transducer in the orientation direction each time the transmitting ultrasound is generated.

The receiver 103 is a circuit which receives an electric receiving signal through the cable 1c from the ultrasound transducer 1b according to control of the controller 108. For example, the receiver 103 includes an amplifier, an A/D (Analog to Digital) converting circuit, and a phase adder circuit. The amplifier is a circuit which amplifies the received signal at a preset amplifying rate for each individual path corresponding to each transducer. The A/D converting circuit is a circuit for A/D conversion of the amplified receiving signal. The phase adder circuit is a circuit for providing delaying time and adjusting the phase on the A/D converted receiving signal for each individual path corresponding to each transducer, and adds (phase adding) the above to generate the sound ray data.

According to control by the controller 108, the image generator 104 performs an envelope detection process and logarithmic amplifier on the sound ray data from the receiver 103, performs adjustment of the dynamic range and gain to convert the brightness, and generates B (Brightness) mode image data. That is, the B mode image data represents the strength of the receiving signal by brightness. Other than the B mode image data, the image generator 104 may generate A (Amplitude) mode image data, M (Motion) mode image data and ultrasound image data according to the Doppler method.

The image processor 105 includes an image memory 105a including a semiconductor memory such as a DRAM (Dynamic Random Access Memory). According to control by the controller 108, the image processor 105 stores the B mode image data output from the image generator 104 in the image memory 105a in a unit of frames. The image data in the unit of frames may be referred to as ultrasound image data or frame image data. The frame image data stored in the image memory 105a is transmitted to the DSC 106 according to control by the controller 108.

According to control by the controller 108, the DSC 106 performs coordinate conversion on the frame image data received by the image processor 105 to convert the frame image data to image signals, and outputs the image signals to the operation display 107.

The operation display 107 includes a display 107a and a touch panel 107b as a touch operating unit.

A display apparatus such as an LCD (Liquid Crystal Display), a CRT (Cathode-Ray Tube) display, an organic EL (Electronic Luminescence) display, an inorganic EL display and a plasma display can be applied as the display 107a. According to control by the controller 108, the display 107a performs display of the image on the display screen according to the image signal output from the DSC 106.

The touch panel 107b is a pressure-sensitive type (resistance film pressure sensitive type) touch panel on which transparent electrodes are positioned in a grid on a display screen of the display 107a. The touch panel 107b detects the XY coordinates of the pressure point pressed by fingers on the screen as a pressure value, and outputs the detected position signal as the operation signal to the controller 108. The touch panel 107b is not limited to the pressure-sensitive type and may be other types such as a capacitance type.

For example, the controller 108 includes a CPU (Central Processing Unit), a ROM (Read Only Memory), and a RAM (Random Access Memory), various types of process programs such as a system program stored in the ROM are read out and deployed in the RAM, and each unit of the ultrasound diagnostic apparatus 1 is controlled according to the deployed program. The ROM includes a nonvolatile memory such as a semiconductor, and stores a system program corresponding to the ultrasound diagnostic apparatus 1, later-described various process programs such as an ultrasound examination program to function as the ultrasound examination process which can be executed on the system program and various data such as a gamma table. Such programs are stored in a state of a computer-readable program code, and the CPU sequentially executes the operation according to the program code. The RAM forms a work area which can temporarily store various programs executed by the CPU and the data regarding the various programs.

For example, the storage 109 includes a large capacity storage medium such as a HDD (Hard Disk Drive), and stores ultrasound image data generated in the image processor 105, examination image data generated in the preserved image generator 111, and the like.

The communicator 110 includes a LAN adaptor and transmits and receives data between other apparatuses connected through a network N such as a LAN (Local Area Network). The communicator 110 can be connected to a server, a storage apparatus, a printer through the network N, for example.

According to control by the controller 108, the preserved image generator 111 generates examination image data as preserved image data in which later-described measurement result information of a measured distance, body mark, annotation, and patient information are overlapped on the ultrasound image data generated in the image processor 105, and stores the examination image data in the storage 109. Through the communicator 110, the examination image data generated in the preserved image generator 111 is transmitted to and stored in the storage apparatus on the network N, and transmitted to and printed in a printer on the network N.

Regarding each unit included in the ultrasound diagnostic apparatus 1, some or all of the functions of each functional block may be realized by the hardware circuit such as an integrated circuit. For example, the integrated circuit is a LSI (Large Scale Integration), and the LSI is distinguished as IC (Integrated Circuit), system LSI, super LSI, and ultra LSI depending on the integration of the LSI. The method of realizing the integrated circuit is not limited to the LSI and can be realized by a dedicated circuit or a general purpose processor. Alternatively, a reconfigurable processor in which connecting and setting of the circuit cell in a FPGA (Field Programmable Gate Array) or the LSI can be employed. Some or all of the functions of each functional block can be executed by software. In this case, the software is stored in one or more storage medium such as a ROM, optical disk, or hard disk. Such software is executed by the calculation processor.

Figure 3:
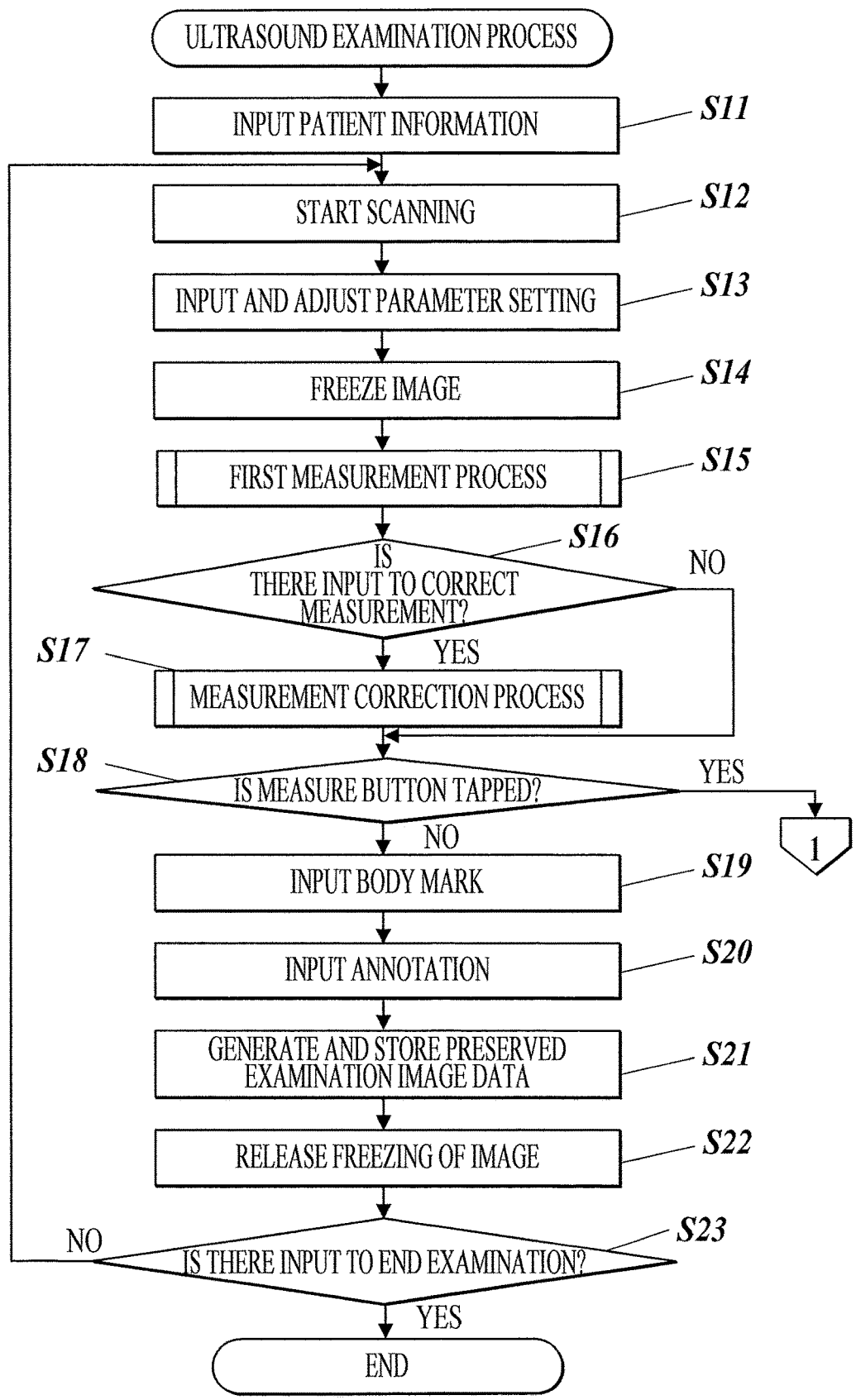
FIG. 3 is a flowchart showing an ultrasound examination process.
Figure 4:
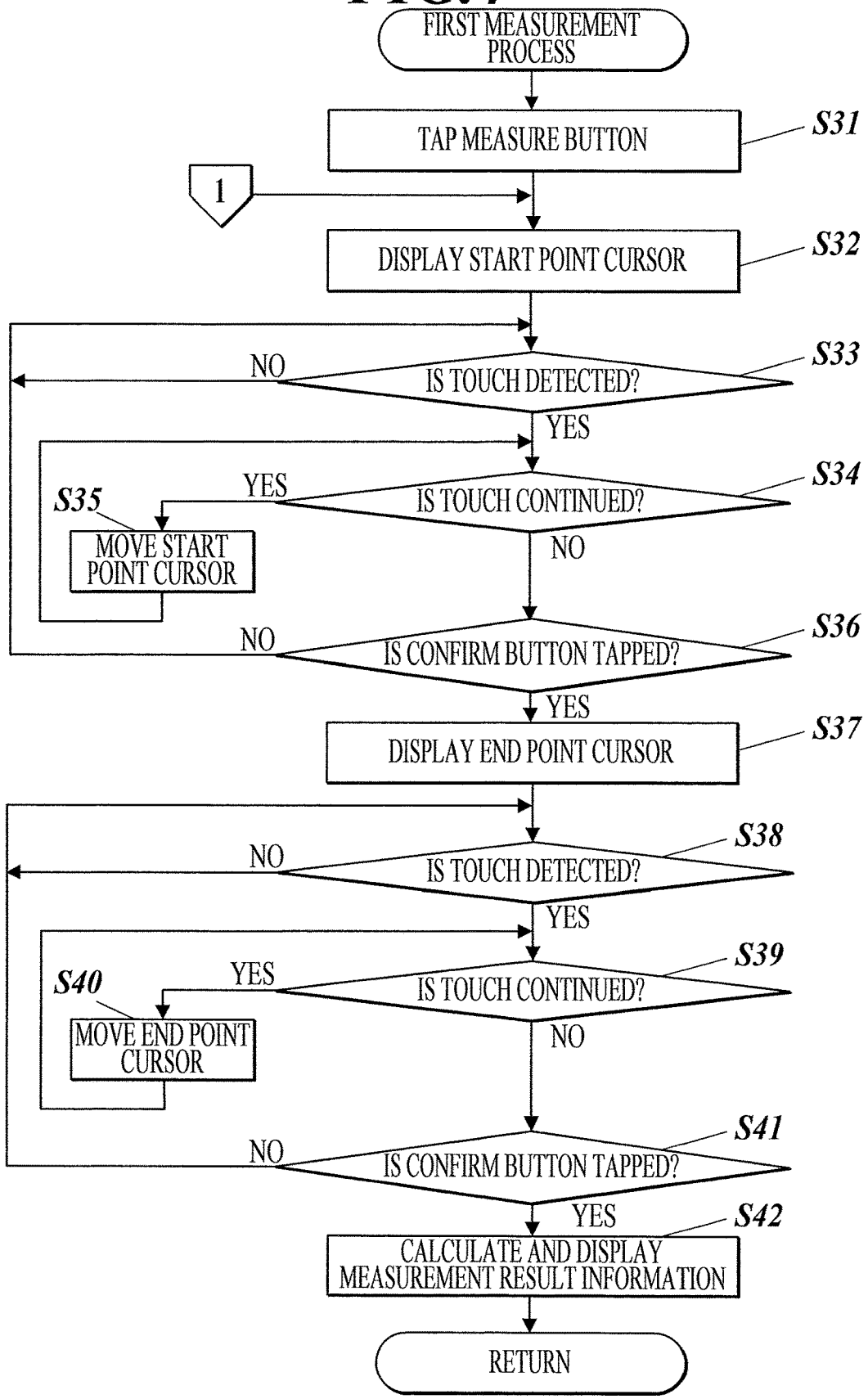
FIG. 4 is a flowchart showing a first measurement process.
Figure 6C:
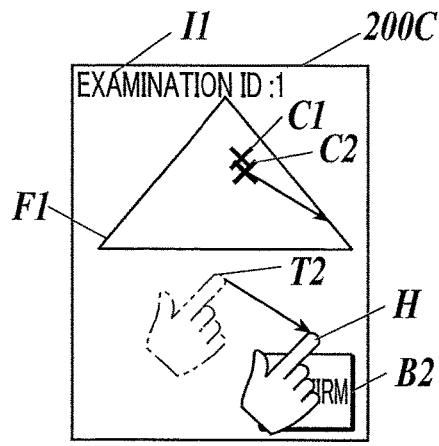
FIG. 6C is a diagram showing a third display screen.
Figure 6D:
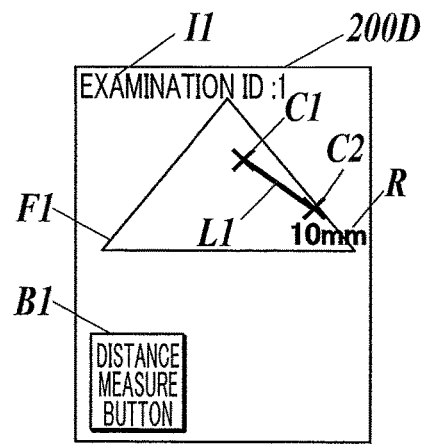
FIG. 6D is a diagram showing a fourth display screen.
Figure 7:
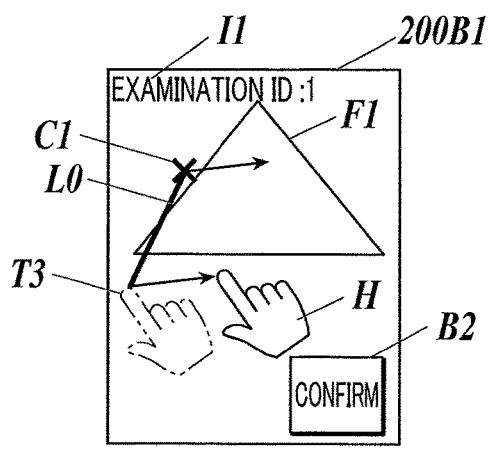
FIG. 7 is a diagram showing a fifth display screen.
Figure 8A:
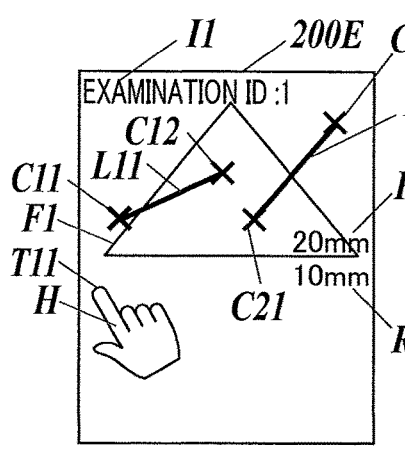
FIG. 8A is a diagram showing a sixth display screen.
Figure 8B:
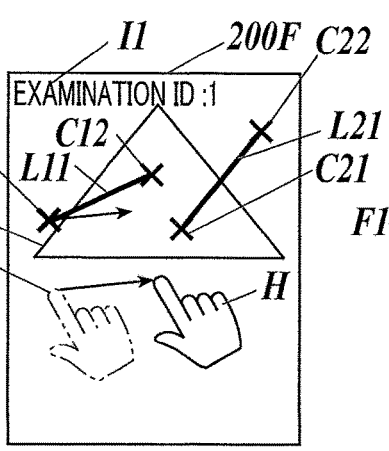
FIG. 8B is a diagram showing a seventh display screen.
Figure 8C:
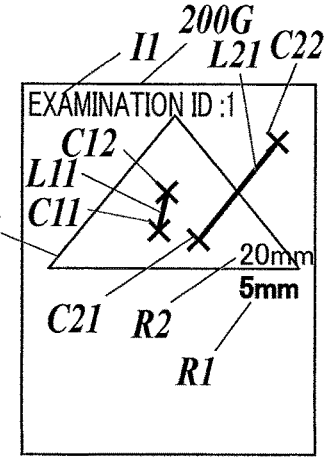
FIG. 8C is a diagram showing an eight display screen.

Next, the operation of the ultrasound diagnostic apparatus 1 is described with reference to FIG. 3 to FIG. 8C. FIG. 3 is a flowchart showing an ultrasound examination process. FIG. 4 is a flowchart showing a first measurement process. FIG. 5 is a flowchart showing a measurement correction process. FIG. 6A is a diagram showing a display screen 200A. FIG. 6B is a diagram showing a display screen 200B. FIG. 6C is a diagram showing a display screen 200C. FIG. 6D is a diagram showing a display screen 200D. FIG. 7 is a diagram showing a display screen 200B1. FIG. 8A is a diagram showing a display screen 200E. FIG. 8B is a diagram showing a display screen 200F. FIG. 8C is a diagram showing a display screen 200G.

The ultrasound examination process performed in the ultrasound diagnostic apparatus 1 is described. According to the ultrasound examination process, the patient as the subject is scanned and the ultrasound image data is displayed. Moreover, as the subject feature amount, the length (distance) of the lesion as the measurement target is measured, and the ultrasound image data including the measurement result information is stored. The measurement target may be a portion other than the lesion, for example, organs of the subject.

The ultrasound diagnostic apparatus 1 is positioned in the diagnosis room of the medical facility in advance, and the patient, and the operator such as the physician, or technician enter the diagnosis room. According to the ultrasound diagnostic apparatus 1, for example, the operator inputting the instruction to execute the ultrasound examination process through the operation input unit 101 acts as a trigger, and the CPU of the controller 108 performs the ultrasound examination process according to the ultrasound examination program stored in the ROM.

As shown in FIG. 3, first, the controller 108 receives input of the patient information such as patient ID, patient name of the patient as the subject from the operator through the operation input unit 101 or the touch panel 107b (step S11). When the patient information input in step S11 is finished, the operator holds the ultrasound probe 1b, places the ultrasound probe 1b against the examination portion of the subject, and starts scanning. Then, through the operation/input unit 101 or the touch panel 107b, the ultrasound diagnosis mode (here, the B mode), and the setting information of the ultrasound image display format are input. Then, according to the input setting information, the controller 108 controls the transmitter 102 to generate the driving signal so that the driving signal is input to the ultrasound probe 1b and the ultrasound is transmitted. The controller 108 controls the receiver 103 to receive the receiving signal according to the reflecting ultrasound (echo) from the subject received by the ultrasound probe 1b so that the ultrasound image data (B mode image data) is generated in the image generator 104 according to the receiving signal. The controller 108 controls the display 107a to display the above through the image processor 105 and the DS 106, and the scanning is started (step S12). After step S12, the ultrasound image (B mode image) is displayed in real time (live) on the display 107a.

Then, the controller 108 receives the input of the image display parameter from the operator through the operation input unit 101 or the touch panel 107b according to necessity, and adjusts each unit for ultrasound image display in the ultrasound diagnostic apparatus main body 1a according to the input image display parameter (step S13). The image display parameter includes display depth, gain, etc.

After step S13, the operator inputs a freeze instruction of the ultrasound image by operating the operation input unit 101 in a state in which the operator scans with the ultrasound probe 1b while displaying the desired ultrasound image. Through the operation input unit 101 or the touch panel 107b, the controller 108 receives input of the freeze instruction of the ultrasound image from the operator, and according to the input freeze instruction, the controller 108 controls each unit to freeze the display of the ultrasound image in the ultrasound diagnostic apparatus main body 1a, and the frozen ultrasound image data is displayed on the display 107a (step S14).

Then, the controller 108 performs a first measurement process which measures a length of the measurement subject such as a lesion of the subject (step S15). For example, as a typically widely used measurement of a length, the first measurement process is a process which measures a straight line between two points by setting the position of the cursor of the start point and the end point as a movement operation element and calculates the straight line distance between two points.

Here, the first measurement process of step S15 is described with reference to FIG. 4. As shown in FIG. 4, first, the controller 108 displays the initial display screen for ultrasound examination on the display 107a, and receives tap input of the measure button B1 from the operator through the touch panel 107b (step S31). The initial display screen includes at least the ultrasound image according to the ultrasound image data frozen in step S14 and the measure button. For example, the display screen 200A shown in FIG. 6A is displayed. The display screen 200A includes examination information I1, an ultrasound image F1, and measure button B1. The examination information I1 includes an examination ID. The ultrasound image F1 is a schematic diagram. The measure button B1 is a button to receive tap input to start measurement.

Then, the controller 108 displays on the display 107a a provisional start point cursor corresponding to the measurement start point (step S32). In step S32, for example, the display screen 200B shown in FIG. 6B is displayed. The display screen 200B is a display screen in which the measure button B1 is erased from the display screen 200A in response to the tap input of the measure button B1, and a start point cursor C1 and a confirm button B2 are further displayed. The confirm button B2 is a button to receive tap input of confirming the setting of the position of the start point cursor or the end point cursor.

Then, the controller 108 determines whether the touching input to the region including the ultrasound image with the exception of the start point cursor on the display screen is received from the operator through the touch panel 107b and whether touching is detected or not (step S33). As shown in the display screen 200B, the operator touches a touch position T1 as a free position in the region including the ultrasound image F1 with the exception of the start point cursor C1 with a finger of a hand H, and by continuing touching and sliding, the start point cursor C1 can be moved while maintaining the relation of the relative position between the start point cursor C1.

When the touching is not detected (step S33; NO), the process advances to step S33. When the touching is detected (step S33; YES), the controller 108 determines whether the touching is continued (sliding is input) according to touch input from the operator through the touch panel 107b (step S34).

When the touching continues (step S34; YES), the controller 108 moves the start point cursor C1 to maintain the relative position relation between the position of the start point cursor and the touch position of the finger of the hand of the operator in response to the sliding input from the operator through the touch panel 107b (step S35), and the process advances to step S34.

When the finger of the hand H of the operator separates from the display screen and the touching is not continued (step S34; NO), the controller 108 determines whether the tap input of the confirm button B2 is received from the operator through the touch panel 107b and the confirm button B2 is tapped (step S36). When the confirm button B2 is not tapped (step S36; NO), the process advances to step S33. When the confirm button B2 is tapped (step S36; YES), the controller 108 confirms the position of the start point cursor and displays on the display 107a a provisional end point cursor corresponding to the measurement end point (step S37). In step S37, for example, the display screen 200C shown in FIG. 6C is displayed. According to the display screen 200C, an end point cursor C2 is added to the display screen 200B including the start point cursor C1 after movement.

Then, the controller 108 determines whether the touch input to the region including the ultrasound image with the exception of the end point cursor on the display screen is received from the operator through the touch panel 107b, and whether the touching is detected (step S38). As shown in the display screen 200C, the operator touches a touch position T2 as a free position in the region including the ultrasound image F1 with the exception of the end point cursor C2 with a finger of a hand H, and by continuing touching and sliding, the end point cursor C2 can be moved while maintaining the relation of the relative position between the end point cursor C2.

When the touching is not detected (step S38; NO), the process advances to step S38. When the touching is detected (step S38; YES), the controller 108 determines whether the touching is continued according to touch input from the operator through the touch panel 107b (step S39).

When the touching continues (step S39; YES), the controller 108 moves the end point cursor C2 to maintain the relative position relation between the position of the end point cursor and the touch position of the finger of the hand of the operator in response to the sliding input from the operator through the touch panel 107b (step S40), and the process advances to step S39.

When the finger of the hand H of the operator separates from the display screen and the touching is not continued (step S39; NO), the controller 108 determines whether the tap input of the confirm button B2 is received from the operator through the touch panel 107b and the confirm button B2 is tapped (step S41). When the confirm button B2 is not tapped (step S41; NO), the process advances to step S38.

When the confirm button B2 is tapped (step S41; YES), the controller 108 confirms the position of the end point cursor, calculates the straight line distance between the start point cursor and the end point cursor, and displays the calculated straight line distance as the measurement result information on the display 107a (step S42). With this, the first measurement process ends. In step S42, for example, the display screen 200D shown in FIG. 6D is displayed. According to the display screen 200D, the positions of the start point cursor C1 and the end point cursor C2 are confirmed in response to the tap input of the confirm button B2 in the display screen 200C, the confirm button B2 is erased, a straight line portion L1 connecting the start point cursor C1 and the end point cursor C2, and measurement result information R which is the length of the straight line portion L1 are further displayed, and the measure button B1 is displayed again.

In step S32, instead of the display screen 200B, the display screen 200B1 shown in FIG. 7 may be displayed. The display screen 200B1 is similar to the display screen 200B, but a straight line portion L0 is displayed between the touch position T3 by the finger of the hand H of the operator and the start point cursor C1 as a display component to associate a touch position T3 and a position of the start point cursor C1. That is, even if the touch position T3 by the finger of the hand H of the operator moves, the relative position between the touch position T3 and the start point cursor C1 does not change. Therefore, the start point cursor C1 is moved without changing the length and the tilt of the straight line portion L0. In step S37, the straight line portion L0 may be displayed between the touch position by the finger of the hand H of the operator and the position of the end point cursor C2. The display component to associate the touch position and the cursor position is not limited to the straight line portion and other shapes such as an arrow can be used.

Returning to FIG. 3, after step S15, the controller 108 determines whether the input of the instruction of correcting the measurement of the step S15 is received from the operator through the operation input unit 101 or the touch panel 107b, and whether the instruction of the measurement correction is input in response to the input (step S16). When the instruction to correct the measurement is input (step S16; YES), the controller 108 performs the measurement correction process to correct the measurement of step S15 (step S17).

Here, with reference to FIG. 5, the measurement correction process of step S17 is described. As shown in FIG. 5, first, the controller 108 determines whether the touch input to the region including the ultrasound image other than the start point cursor and the end point cursor of the display screen is received from the operator through the touch panel 107b and whether the touching is detected (step S51). When the touching is not detected (step S51; NO), the process advances to step S51.

When the touching is detected (step S51; YES), the controller 108 detects a start point cursor or an end point cursor nearest to the touch position input in step S51 as a control target cursor (step S52). In step S52, for example, after step S15 is performed two times, a display screen 200E shown in FIG. 8A is displayed. The display screen 200E includes, examination information I1, ultrasound image F1, the following displayed in the first measurement which are start point cursor C11, end point cursor C12, straight line portion L11, measurement result information R1, and the following displayed in the second measurement which are start point cursor C21, end point cursor C22, straight line portion L21, and measurement result information R2.

As shown in the display screen 200E, when the operator uses the finger of the hand H to touch a touch position T11 which is any position in the region including the ultrasound image F1 with the exception of the start point cursors C11, C21 and the end point cursors C12, C22, the start point cursor C11 nearest to the touch position T11 is detected as the control target cursor, and is displayed actively.

Then, the controller 108 determines whether the touching continues (slide input) by the touch input from the operator through the touch panel 107b (step S53). When the touching continues (step S53; YES), in response to the slide input from the operator through the touch panel 107b, the controller 108 moves the control target cursor to maintain the relative position relation between the position of the control target cursor and the touch position of the finger of the hand of the operator (step S54), and the process advances to step S53. For example, in step S54, the display screen 200F shown in FIG. 8B is displayed. In the display screen 200F, the finger of the hand H of the operator continues touching and sliding on the display screen 200E, and the start point cursor C11 is moved while maintaining the relative position relation between the position of the start point cursor C11 as the control target cursor and the touch position T11.

When the touching is not continued (finger is released) (step S53; NO), the controller 108 confirms the position of the control target cursor moved in step S54 (step S55). Then, the controller 108 calculates the straight line distance between the control target cursor confirmed in step S55 and the cursor (start point cursor or end point cursor) corresponding to the control target cursor (in which the start point or the end point is opposite), updates and displays the calculated straight line distance as the measurement result information on the display 107a (step S56) and ends the measurement correction process. In step S56, for example, the display screen 200G shown in FIG. 8C is displayed. The display screen 200G shows that the start point cursor C11 as the control target cursor is moved and determined in the display screen 200F, and the measurement result information R1 of the distance between the start point cursor C11 and the end point cursor C12 corresponding to the start point cursor C11 is updated from "10 mm", to "5 mm".

Returning to FIG. 3, the controller 108 determines whether tap input of the measure button B1 is received from the operator through the touch panel 107b to instruct to perform the first measurement process of step S15 again, and determines whether the measure button B1 is tapped (step S18). When the instruction to correct the measurement is not input (step S16; NO), the process advances to step S18. When the measure button B1 is tapped (step S18; YES), the process advances to step S32 to perform the first measurement process again.

When the measure button. B1 is not tapped (step S18; NO), the first measurement process and the measurement correction process ends, and the controller 108 receives input of a body mark from the operator through the operation input unit 101 (step S19). The body mark is a mark set in the ultrasound image data for the operator to show the ultrasound image obtaining portion of the subject (scanning portion, observing portion) or the information regarding the ultrasound probe 1b position during scanning. The body mark is overlapped in the ultrasound image of the display screen or the region other than the above.

Then, the controller 108 receives input of annotation from the operator through the operation input unit 101 (step S20). The annotation is text information regarding the ultrasound image of the subject in the ultrasound image data. The annotation can be any character input on the keyboard or a string of characters of a selected reserved word prepared in advance, and can be overlapped on the ultrasound image of the display screen or in the region other than the above.

Then, the controller 108 obtains the ultrasound image data frozen in step S14 from the image processor 105. The controller 108 controls the preserved image generator 111 to generate examination image data overlapping on the obtained ultrasound image data the following, the start point cursor, end point cursor, straight line portion and measurement result information measured in step S15 or corrected in step S17, the body mark input in step S19, the annotation input in step S20, and patient information and examination information input in step S11. The examination image data is stored in the storage 109 (step S21).

Then, the controller 108 releases the freezing in step S14, controls each unit of the ultrasound diagnostic apparatus main body 1a to display release of the freezing of the ultrasound image and displays the live ultrasound image of the subject (step S22). Then, it is determined whether the input of the instruction to end the examination is received from the operator through the operation input unit 101, and whether the instruction to end the examination is input (step S23). When the instruction to end the examination is not input (step S23; NO), the process advances to step S12. When the instruction to end the examination is input (step S23; YES), the ultrasound examination process ends. By repeating the process of steps S12 to S23, plurality of sets of examination image data are stored for one patient.

According to the above-described embodiment, the ultrasound diagnostic apparatus 1 includes a touch panel 107b which receives touch input on the display screen of the display 107a which displays the ultrasound image and a controller 108 which moves the start point cursor and the end point cursor in response to touch input to the region including the ultrasound image with the exception of the start point cursor and the end point cursor displayed on the display screen.

Therefore, since the start point cursor and the end point cursor are not directly touched, the start point cursor and the end point cursor are not hidden by the finger and the start point cursor and the end point cursor can be moved to the accurate position. With this, it is possible to control touch operation in the position preferred by the operator for the start point cursor and the end point cursor (not in the fixed region such as the touch pad) without losing intuitive operation of the touch operation (operation by arrow buttons showing up, down, left, and right is not intuitive). Therefore, intuitive operation by touch to the predetermined position can enhance the operability and accuracy of movement of the start point cursor and the end point cursor.

The controller 108 moves the start point cursor and the end point cursor maintaining the relative position relation between the position of the start point cursor and the end point cursor and the touch position, in response to the slide input to the region including the ultrasound image with the exception of the start point cursor and the end point cursor. Therefore, the operability and the accuracy of the movement of the start point cursor and the end point cursor can be enhanced according to the operation of the operator.

The controller 108 detects as the control target the start point cursor and the end point cursor in the position (nearest) corresponding to the touch position in response to the first touch input to the region including the ultrasound image with the exception of the plurality of start point cursors and the end point cursors displayed on the display screen. In response to the second touch input after the first touch input, the controller 108 moves the start point cursor and the end point cursor as the control target. Therefore, the desired cursor can be easily selected from the plurality of cursors, and then moved. The position corresponding to the touch position is not limited to the position nearest to the touch position, and may be other positions corresponding to the touch position such as positions at a predetermined distance from the touch position or in a predetermined direction from the touch position.

The controller 108 displays on the display 107a a straight line portion L0 which associates the start point cursor or the end point cursor with the touch position according to the touch input. Therefore, the operator is able to easily and clearly understand visually where the control target cursor is.

The controller 108 calculates the length of the measurement target of the ultrasound image according to the position of the start point cursor and the end point cursor. Therefore, the length of the measurement target of the subject can be obtained easily and accurately according to the position of the start point cursor and the end point cursor.

The controller 108 displays the start point cursor and the end point cursor on the display 107a in response to the tap input of the measure button as the predetermined operation before starting the movement. Therefore, the operator is able to input by touch on the predetermined position while referring to the position of the temporary cursor.

Second Embodiment

The second embodiment of the present invention is described with reference to FIG. 9 to FIG. 11C. Similar to the first embodiment, the ultrasound diagnostic apparatus 1 is used as the apparatus of the present embodiment. However, a later described second measurement process is stored as the ultrasound examination program in the ROM of the controller 108 of the ultrasound diagnostic apparatus 1 instead of the first measurement process of step S15 shown in FIG. 3.

Figure 9:
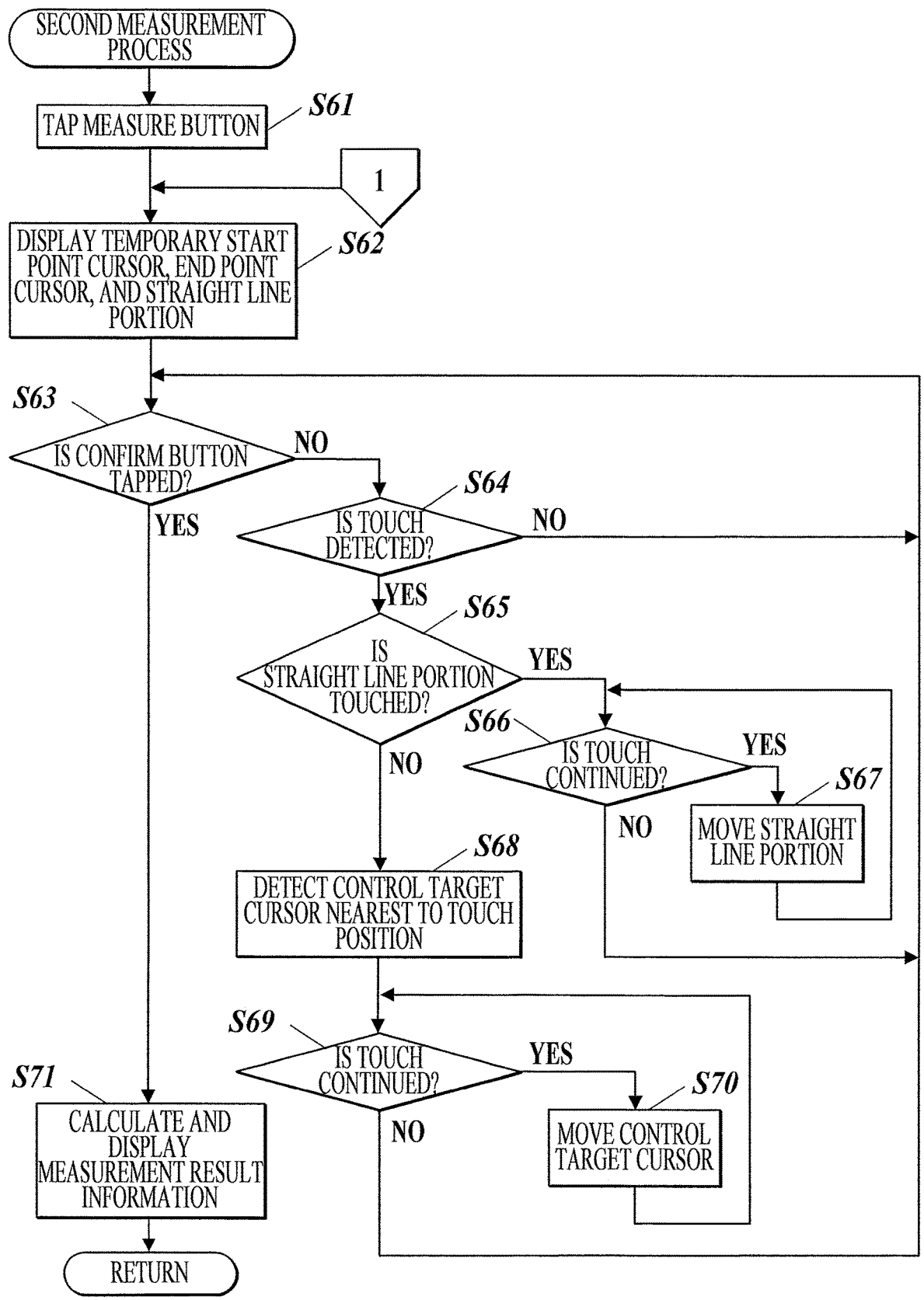
FIG. 9 is a flowchart showing a second measurement process.
Figure 10A:
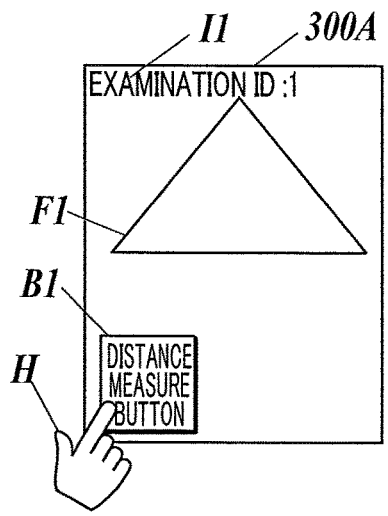
FIG. 10A is a diagram showing a ninth display screen.
Figure 10B:
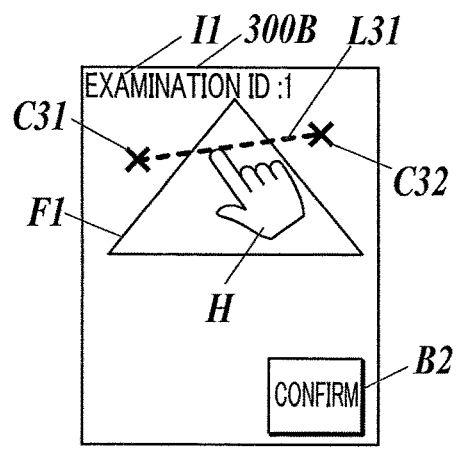
FIG. 10B is a diagram showing a tenth display screen.
Figure 10C:
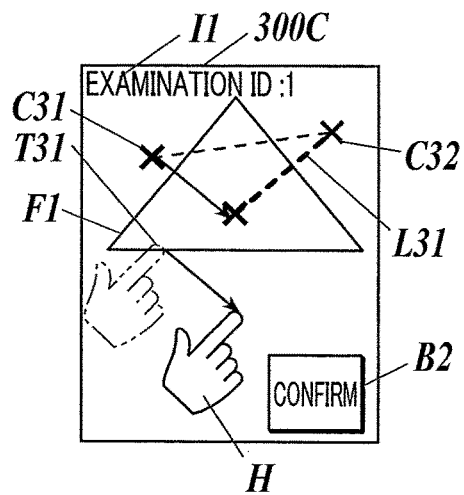
FIG. 10C is a diagram showing an eleventh display screen.
Figure 10D:
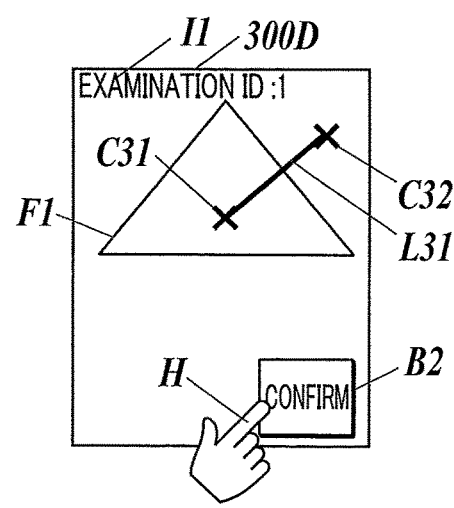
FIG. 10D is a diagram showing a twelfth display screen.
Figure 11A:
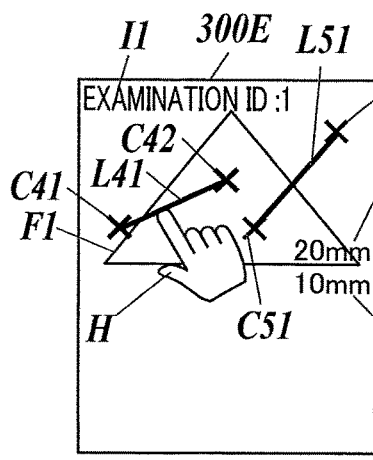
FIG. 11A is a diagram showing a thirteenth display screen.
Figure 11B:
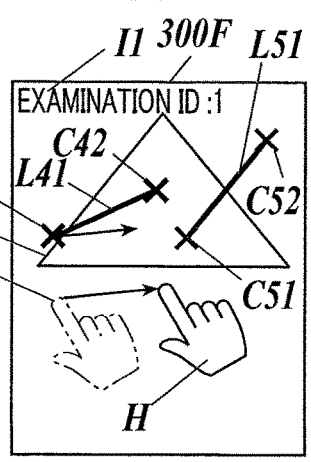
FIG. 11B is a diagram showing a fourteenth display screen.
Figure 11C:
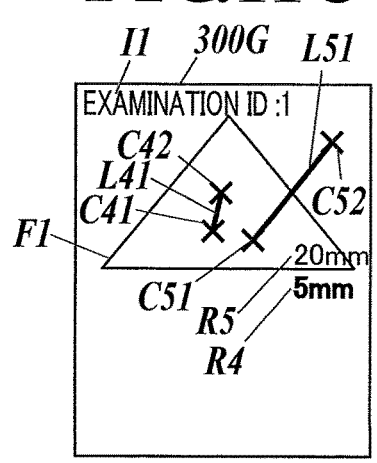
FIG. 11C is a diagram showing a fifteenth display screen.

Next, the operation of the ultrasound diagnostic apparatus 1 is described with reference to FIG. 9 to FIG. 11C. FIG. 9 is a flowchart showing the second measurement process. FIG. 10A is a diagram showing a display screen 300A. FIG. 10B is a diagram showing a display screen 300B. FIG. 10C is a diagram showing a display screen 300C. FIG. 10D is a diagram showing a display screen 300D. FIG. 11A is a diagram showing a display screen 300E. FIG. 11B is a diagram showing a display screen 300F. FIG. 11C is a diagram showing a display screen 300G.

Here, in order to avoid redundant description, the second measurement process performed instead of the first measurement process in the ultrasound examination process performed in the ultrasound diagnostic apparatus 1 is described. As shown in FIG. 9, first, step S61 is similar to step S31 of the first measurement process. For example, in step S61, the display screen 300A shown in FIG. 10A is displayed. The display screen 300A includes examination information I1, ultrasound image F1, and measure button B1.

Then, the controller 108 displays on the display 107a the temporary start point cursor and temporary end point cursor (the positions are not determined) and the straight line portion between the start point cursor and the end point cursor (step S62). In step S62, for example, the display screen 300B shown in FIG. 10B is displayed. In the display screen 300B, the start point cursor C31, the end point cursor C32, and the straight line portion L31 as the caliper rod and the confirm button B2 are added to the display screen 300A. The straight line portion L31 is a straight line portion to connect the start point cursor C31 and the end point cursor C32.

Then, the controller 108 determines whether the tap input of the confirm button B2 is received from the operator through the touch panel 107b, and whether the confirm button B2 is tapped (step S63). When the confirm button B2 is not tapped (step S63; NO), the controller 108 determines whether the tap input on the region including the ultrasound image F1 with the exception of the start point cursor C31 and the end point cursor C32 on the display screen is received from the operator through the touch panel 107b, and whether the touching is detected (step S64). As shown in the display screen 300B, the operator uses the finger of the hand H to touch the straight line portion L31 of the region including the ultrasound image F1 with the exception of the start point cursor C31 and the end point cursor C32, and continues the touching and slides to move the straight line portion L31 parallel. The operator uses the finger of the hand H to touch the position other than the straight line portion L31 of the region including the ultrasound image F1 with the exception of the start point cursor C31 and the end point cursor C32 and continues touching and slides to move the nearest control point (start point cursor C31 or end point cursor C32).

When the touching is not detected (step S64; NO), the process advances to step S63. When the touching is detected (step S64; YES), the controller 108 determines whether the straight line portion in the display of step S64 is touched (step S65). When the straight line portion is touched (step S65; YES), the controller 108 determines whether the touch continues (slide input) by touch input from the operator through the touch panel 107b (step S66).

When the touching continues (step S66; YES), the controller 108 moves the straight line portion parallel in response to the slide input from the operator through the touch panel 107b (step S67), and the process advances to step S66. For example, in step S67, as shown in the display screen 300B, the straight line portion L31 is moved parallel with the slide input by the finger of the hand H of the operator on the straight line portion L31. When the touching is not continued (finger is separated) (step S66; NO), the process advances to step S63.

When the straight line portion is not touched (step S65; NO), the controller 108 detects the start point cursor of the end point cursor nearest to the touch position input in step S64 as the control target cursor (step S68). For example, in step S68, the display screen 300C shown in FIG. 10C is displayed. The display screen 300C shows that the finger of the hand H of the operator touches the touch position T31 after the position of the straight line portion L31 is confirmed in the display screen 300B.

As shown in the display screen 300C, the operator uses the finger of the hand H to touch the touch position T31 as the free position in the region including the ultrasound image F1 with the exception of the start point cursor C31 and the end point cursor C32, the start point cursor C31 nearest to the touch position T31 is detected as the control target cursor, and is displayed actively.

Then, the controller 108 determines whether the touch continues (slide input) by the touch input from the operator through the touch panel 107b (step S69). When the touch continues (step S69; YES), the controller 108 moves the control target cursor to maintain the relative position relation between the position of the control target cursor and the touch position of the finger of the hand H of the operator in response to the slide input from the operator through the touch panel 107b (step S70), and the process advances to step S69. For example, in step S70, the display screen 300C is displayed, and the touch by the finger of the hand H of the operator is continued and slides in the display screen 300C. With this, the start point cursor C31 is moved while maintaining the relative position relation between the position of the start point cursor C31 as the control target cursor and the touch position T11.

When the touching is not continued (step S69; NO) the process advances to step S63. As described above, according to steps S63 to S70, the position of one control target cursor (start point cursor C31) is set, and steps S63 to S70 are repeated to set the position of another corresponding control target cursor (end point cursor C32) as necessary. Here, for example, the display screen 300D shown in FIG. 10D is displayed. According to the display screen 300D, the positions of the start point cursor C31 and the end point cursor C32 in the display screen 300C are set and the hand H of the operator receives the tap input of the confirm button B2.

When the confirm button B2 is tapped (step S63; YES), the controller 108 confirms the positions of the start point cursor C31 and the end point cursor C32, calculates the straight line distance between the confirmed start point cursor C31 and the end point cursor C32, displays the calculated straight line distance as the measurement result information on the display 107a (step S71), and the second measurement process ends. The display screen displayed in step S71 is the display screen in which, in response to the tap input of the confirm button B2, in the display screen 300D, the positions of the start point cursor C31 and the end point cursor C32 are confirmed, the confirm button B2 is erased, the straight line portion L31 which connects the start point cursor C31 and the end point cursor C32, and the measurement result information which is the length of the straight line portion L31 are further displayed, and the measure button B1 is displayed again.

The measurement correction process of step S17 of the ultrasound examination process may be the measurement correction process shown in FIG. 5 or may be the measurement correction process as the modification shown below. For example, the display screen 300E shown in FIG. 11A is displayed before step S17. The display screen 300E includes the examination information I1, the ultrasound image F1, the following which are displayed in the first measurement, the start point cursor C41, the end point cursor C42, the straight line portion L41, and the measurement result information R4, and the following which are displayed in the second measurement, the start point cursor C51, the end point cursor C52, the straight line portion L51, and the measurement result information R5.

As shown in the display screen 300E, the operator uses the finger of the hand H to input by touch the straight line portion L41 of the region including the ultrasound image F1 with the exception of the start point cursors C41, C51 and the end point cursors C42, C52. According to the measurement correction process of the modification, the steps similar to steps S63 to S67 shown in FIG. 9 are performed, and the straight line portion L41 is moved parallel by the slide input of the operator. Then, the steps similar to the measurement correction process shown in FIG. 5 are performed.

For example, the display screen 300F shown in FIG. 11B is displayed. In the display screen 300F, after the position of the straight line portion L41 is set in the display screen 300E, the touch position T41 is input by touching with the finger of the hand H of the operator. Here, among the start point cursor C41 and the end point cursor C42 corresponding to the touched straight line portion L41, the start point cursor C41 nearest to the touch position T41 is to be the control target cursor. The cursor closest to the touch position among all cursors (for example, start point cursors C41, C51 and end point cursors C42, C52) may be the control target cursor.

Then, when the operator continues touching and slides, the start point cursor C41 is moved while maintaining the relative position relation between the position of the start point cursor C41 as the control target cursor and the touch position T41. Then, for example, the display screen 300G shown in FIG. 11C is displayed. The display screen 300G shows in the display screen 300F, the start point cursor C41 as the control target cursor is moved and confirmed, and the measurement result information R4 of the distance between the start point cursor C41 and the end point cursor C42 corresponding to the above is updated from "10 mm" to "5 mm".

When the measure button B1 is tapped (step S18; YES), the process advances to step S62.

According to the above-described embodiment, in response to the tap input of the measure button as the predetermined operation before starting the movement, the controller 108 displays on the display 107a all (pair) of start point cursors and end point cursors used in calculation of the length of the measurement target of the ultrasound image. Therefore, the start point cursor and the end point cursor necessary for calculating the length of the measurement target can be acknowledged by sight in advance.

Third Embodiment

The third embodiment of the present invention is described with reference to FIG. 12 to FIG. 14C. Similar to the first embodiment, the ultrasound diagnostic apparatus 1 is used as the apparatus of the present embodiment. However, a later described third measurement process is stored as the ultrasound examination program in the ROM of the controller 108 of the ultrasound diagnostic apparatus 1 instead of the first measurement process of step S15 shown in FIG. 3.

Figure 12:
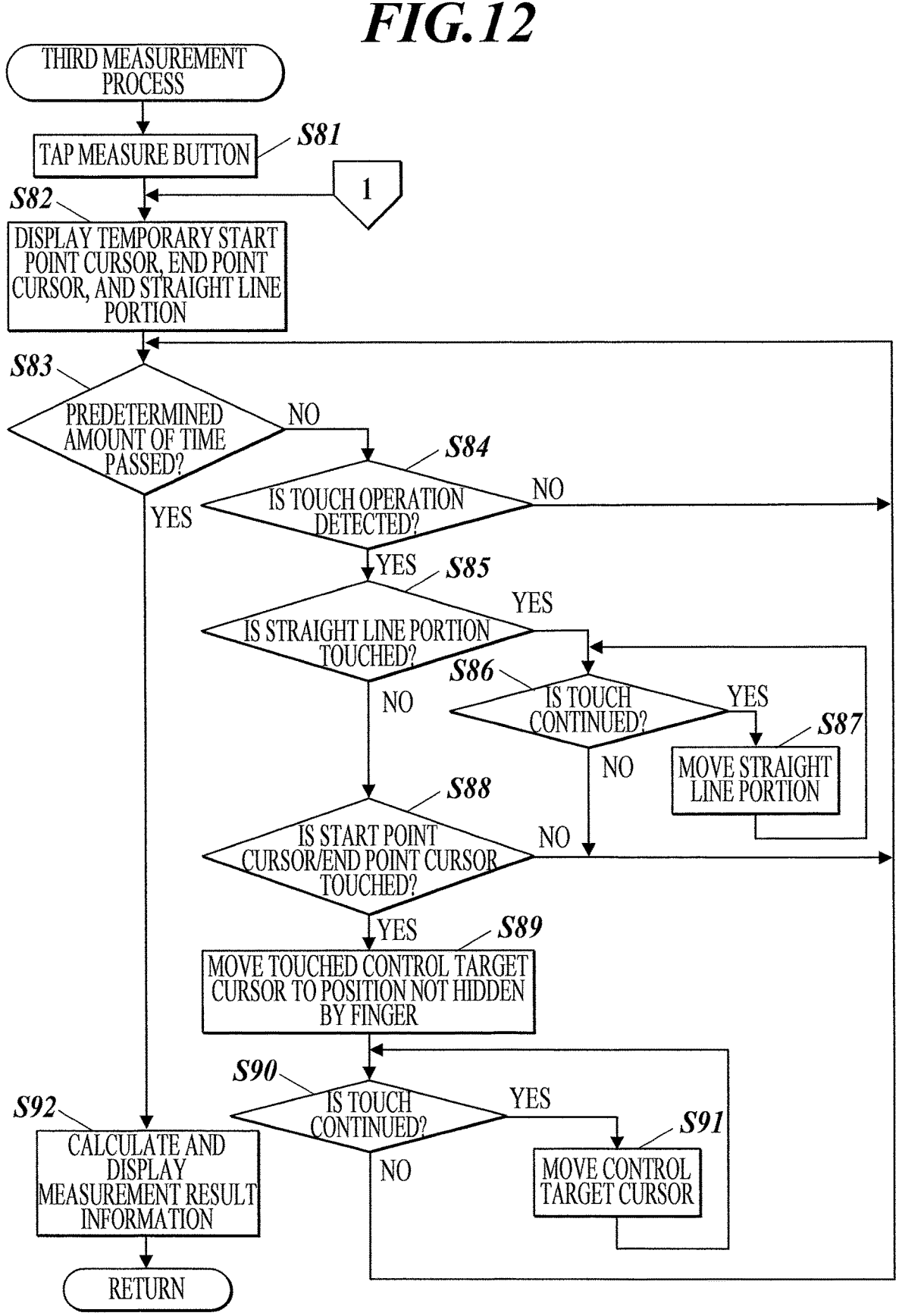
FIG. 12 is a flowchart showing a third measurement process.
Figure 14A:
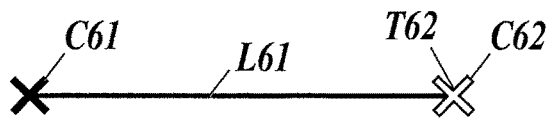
FIG. 14A is a diagram showing a start point cursor, an end point cursor, and a straight line portion.
Figure 14B:
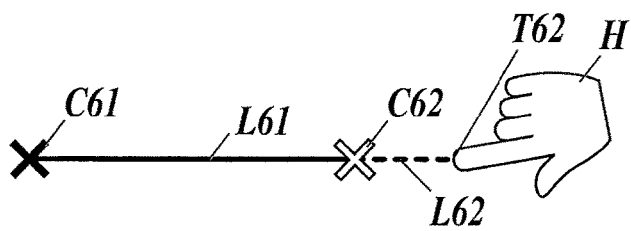
FIG. 14B is a diagram showing a state after touching the end point cursor.
Figure 14C:
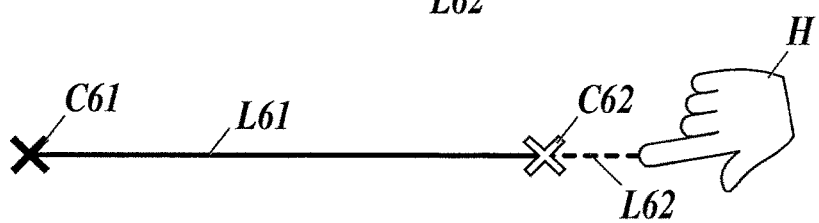
FIG. 14C is a diagram showing a state of sliding the end point cursor.

Next, the operation of the ultrasound diagnostic apparatus 1 is described with reference o FIG. 12 to FIG. 14C. FIG. 12 is a flowchart showing the third measurement process. FIG. 13A is a diagram showing the display screen 400A. FIG. 13B is a diagram showing the display screen 400B. FIG. 13C is a diagram showing the display screen 400C. FIG. 13D is a diagram showing the display screen 400D. FIG. 14A is a diagram showing the start point cursor C61, the end point cursor C62, and the straight line portion L61. FIG. 14B is a diagram showing a state after touching the end point cursor C62. FIG. 14C is a diagram showing a sliding movement of the end point cursor C62.

Here, in order to avoid redundant description, the third measurement process performed instead of the first measurement process in the ultrasound examination process performed in the ultrasound diagnostic apparatus 1 is described. As shown in FIG. 12, first, steps S81, S82 are similar to steps S61, S62 of the second measurement process shown in FIG. 9. In step S82, for example, the display screen 400A shown in FIG. 13A is displayed. The display screen 400A includes the examination information I1, the ultrasound image F1, and the measure button B1.

After step S82, the controller 108 determines whether a predetermined amount of time passed after the last touch operation (step S83). When a predetermined amount of time has not passed (step S83; NO), the process advances to step S84. Steps S84 to S87 are similar to the steps S64 to S67 of the second measurement process.

For example, in steps S84 to S87, the display screen 400B shown in FIG. 13B is displayed. The display screen 400B is a display screen in which in the display screen 400A, the measure button B1 is deleted in response to the tap of the measure button B1, and the start point cursor C61, the end point cursor C62, the straight line portion L62 are further displayed as the caliper rod. As shown in the display screen 400B, the operator uses the finger of the hand H to touch the straight line portion L61 of the region including the ultrasound image F1 with the exception of the start point cursor C61 and the end point cursor C62, and by continuing touching and then sliding, the straight line portion L61 can be moved parallel. For example, by moving the straight line portion L61 parallel, the start point cursor C61 is positioned in the position desired by the operator.

When the straight line portion is not touched (step S85; NO), the controller 108 determines whether the start point cursor or the end point cursor is touched in step S84 (step S88). When the start point cursor or the end point cursor is not touched (step S88; NO), the process advances to step S83.

When the start point cursor or the end point cursor is touched (step S88; YES), the controller 108 moves the start point cursor or the end point cursor touched in step S84 to the position not hidden by the finger of the hand H of the operator as the control target cursor (step S89). Here, with reference to FIG. 14A, FIG. 14B, an example of the operation of step S89 is described.

First, as shown in FIG. 14A, at the point of step S85; NO, the start point cursor C61, the end point cursor C62, and the straight line portion L62 in between are displayed. Then, the end point cursor C62 (position T62) is touched by the finger of the hand H of the operator and after step S88; YES, the process advances to step S89. Then, the touched end point cursor C62 is moved to the corresponding start point cursor C61 side and is hidden by the finger of the hand H. The straight line portion L61 with a solid line becomes short also. A dotted line straight line portion L62 is displayed between the touch position of the finger of the hand H and the end point cursor C62 after movement. With this, for example, in step S89, the display screen 400C shown in FIG. 13C is displayed. In the display screen 400C, the end point cursor C62 of the display screen 400B is touched and is moved to the start point cursor C61 side, and the straight line portion L62 is included also.

Steps 90, 91 are similar to steps S69, S70 shown in the second measurement process. In steps S90, S91, for example, as shown in FIG. 14C, by input of the finger of the hand H of the operator sliding to the opposite side of the start point cursor C61, the end point cursor C62 is moved to the opposite side of the start point cursor C61 maintaining the relation of the relative position (predetermined distance) between the touch position of the finger of the hand H.

After a predetermined amount of time passes (step S83; YES), the process advances to step S92, and the third measurement process ends. Step S92 is similar to step S71 of the second measurement process. For example, in step S83, the display screen 400D shown in FIG. 13D is displayed. The display screen 400D is a display screen in which in the display screen 400C, the positions of the start point cursor C61 and the end point cursor C62 are confirmed, the confirm button B2 is deleted, the straight line portion L61 connecting the start point cursor C61 and the end point cursor C62 and the measurement result information R6 which is the length of the straight line portion L61 are further displayed, and the measure button B1 is displayed again. In response to the finger of the hand H separating, the straight line portion L62 is deleted. By waiting in this state, the predetermined amount of time passes and step S92 is performed.

When the measure button B1 is tapped (step S18; YES), the process advances to step S82.

As described above, according to the present embodiment, when the touch input to the start point cursor or the end point cursor is performed, the controller 108 moves the start point cursor or the end point cursor to a position where the start point cursor or the end point cursor is not hidden by the finger of the hand H of the operator. According to the above-described embodiment, accurate movement of the cursor position is possible by directly touching the cursor which is intuitive operation, and it is possible to prevent weakening of operability by the cursor being hidden by the finger of the hand H and the operator not being able to confirm the cursor by sight.

In response to the slide input after the touch input to the start point cursor or the end point cursor, the start point cursor or the end point cursor is moved while maintaining the relative position relation between the position of the start point cursor or the end point cursor after moving to the position not hidden by the finger of the hand H of the operator and the touch position. Therefore, in response to the operation of the operator, the operability and accuracy of the movement of the start point cursor and the end point cursor can be enhanced.

The embodiments described above are merely one example of the preferable ultrasound diagnostic apparatus according to the present invention, and the present invention is not limited to the above. For example, at least two of the embodiments can be suitably combined.

According to the present embodiment, the touch input is performed by the finger of the hand H of the operator as the operation source, but the present invention is not limited to the above. Touch input can be performed by other operation sources such as a touch pen operated by the operator.

According to the present embodiment, the start point cursor and the end point cursor as the movement operation element is moved, and the straight line distance between the moved start point cursor and the end point cursor is measured but the present invention is not limited to the above. As measurement, other measurement such as trace measurement can be performed. Trace measurement is a process in which the outline of the measurement target such as organs of the subject is automatically traced and surrounded to calculate feature amount to calculate the square area inside the surrounding tracing line and the cubic volume of the measurement target including the tracing line.

Figure 15A:
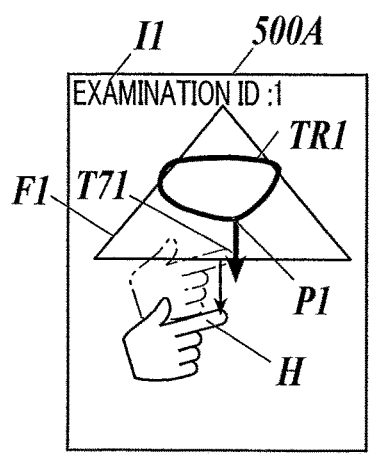
FIG. 15A is a diagram showing a twentieth display screen.
Figure 15B:
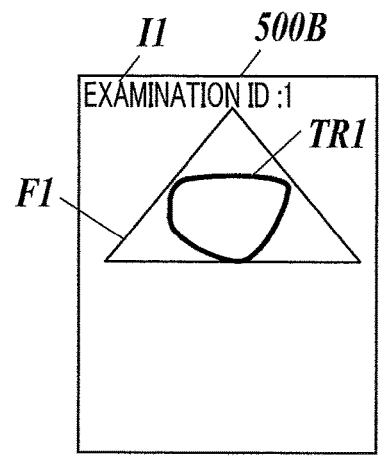
FIG. 15B is a diagram showing a twenty-first display screen.

For example, as shown in FIG. 15A, the ultrasound diagnostic apparatus may perform measurement using the tracing line TR1 as shown in the display screen 500A. FIG. 15A is a diagram showing a display screen 500A. FIG. 15B is a diagram showing a display screen 500B.

The display screen 500A includes examination information I1, ultrasound image F1 and tracing line TR1. The tracing line TR1 is a closed curve in which the measurement target is surrounded by automatic tracing, and is able to move on the display screen. The tracing line TR1 generated by the automatic tracing includes a plurality of points, and similar to straight line measurement, the point P1 closest to the touch position T71 of the touch input by the hand H of the operator is detected as the control target point which is the movement operation element. In response to the slide input by the finger of the hand H, the tracing line TR1 is moved maintaining the relative position relation between the point P1 and the touch position. For example, the display screen 500B shown in FIG. 15B is displayed. The display screen 500B includes the tracing line TR1 after movement. As described above, the result of the automatic tracing (tracing line) can be finely adjusted by the operation the same as the straight line measurement described in the above-described embodiments. The movement operation element which is moved is not limited to the cursors such as the start point cursor and the end point cursor or the tracing line, and can be another movement operation element which can be moved on the display screen by touch operation.

According to the embodiments of the present invention, the movement operation element (cursor) is moved on the region including the ultrasound image as the medical image on the display screen of the ultrasound diagnostic apparatus 1, but the present invention is not limited to the above. For example, the configuration to move the movement operation element on the region including the medical image on the display screen can be applied in the medical image display apparatus displaying other medical images such as a radiation image, endoscope image, thermography, medical picture, microscopic image, and the like.

The movement operation of the cursor as the movement operation element is not limited to slide input and can be other touch input such as tap input of two points of the point before movement and the point after movement.

According to the above-described embodiment, examination image data as the still image data is generated and kept, but the present invention is not limited to the above. A structure similar to the above-described embodiment which moves the movement operation element by operation according to input by touch and which generates and stores moving image data of the subject may be employed.

According to the above-described embodiments, the control target cursor moves in response to slide input by the operator while maintaining the relative position relation between the position of the control target cursor (start point cursor or end point cursor) and the touch position of the finger of the hand of the operator, but the present invention is not limited to the above. For example, the movement amount of the control target cursor may be different from the movement amount of the finger of the hand performing the sliding input of the operator. Specifically, the movement amount of the finger of the hand input with sliding by the operator is set larger than the movement amount of the control target cursor. With this, fine adjustment of the position of the movement amount of the control target cursor can be easily performed.

The detailed configuration and operation of each unit composing the ultrasound diagnostic apparatus 1 of the present embodiment can be suitably modified without leaving the scope of the present invention.

Although embodiments of the present invention have been described and illustrated in detail, the disclosed embodiments are made for purposes of illustration and example only and not limitation. The scope of the present invention should be interpreted by terms of the appended claims.

The entire disclosure of Japanese Patent Application No. 2017-003758 filed on Jan. 13, 2017 is incorporated herein by reference in its entirety.

What is claimed is:
1. A medical image display apparatus comprising:
a touch screen display configured to receive a touch input on a display screen which displays a medical image; and
a display controller configured to:
control the display screen to display a plurality of cursors;
after the plurality of cursors are displayed, and in response to a touch input at a touch position that is (i) in a region of the touch screen display including the medical image and (ii) spaced apart from the plurality of cursors displayed on the display screen, detect which one of the plurality of cursors on the display screen is closest to the touch position, and set the detected one of the plurality of cursors as a control target cursor; and after setting the detected one of the plurality of cursors as the control target cursor, perform a movement operation on the control target cursor on the display screen in response to a sliding touch operation input to the touch screen display, to move the control target cursor while maintaining a relative distance between the touch position and the control target cursor which is spaced apart from the touch position.

2. The medical image display apparatus according to claim 1, wherein the display controller is further configured to control the display screen to display a display element in addition to the plurality of cursors, the display element associating a position of the control target cursor with the touch position of the touch input.

3. The medical image display apparatus according to claim 1, wherein the display controller is configured to control the display screen to begin display of a first one of the plurality of cursors in response to a predetermined operation.

4. The medical image display apparatus according to claim 1, wherein the display controller is configured to control the display screen to simultaneously begin display of a number of the cursors to be used in a calculation of a feature amount of a measurement target in the medical image in response to a predetermined operation.

5. The medical image display apparatus according to claim 1, wherein the display controller is further configured to:

in response to a touch input directly on one of the plurality of cursors, move said one of the plurality of cursors to a position where said one of the plurality of cursors is not hidden by an operation source of the touch input, and such that said one of the plurality of cursors is spaced apart from the touch position of the touch input.

6. The medical image display apparatus according to claim 5, wherein the display controller is further configured to:

after moving said one of the plurality of cursors to the position where said one of the plurality of cursors is not hidden by the operation source of the touch operation, control movement of said one of the plurality of cursors in response to a sliding touch operation input to the touch screen display, to move said one of the plurality of cursors while maintaining a relative distance between the touch position and said one of the plurality of cursors spaced apart from the touch position.

7. The medical image display apparatus according to claim 1, further comprising a calculator which calculates a feature amount of a measurement target of the medical image according to positions of the plurality of cursors.

8. The medical image display apparatus according to claim 1, wherein the display controller is configured to:

control the display screen to display an operation button for beginning a measurement operation; and in response to a user touch operation on the operation button, control the display screen to simultaneously display said plurality of cursors and a line connecting said plurality of cursors at temporary positions to be adjusted by a user.

* * * * *